United States Patent [19]

Steer

[11] Patent Number: 4,892,530
[45] Date of Patent: Jan. 9, 1990

[54] OSTOMY COUPLING

[75] Inventor: Peter L. Steer, Surrey, England

[73] Assignee: Edward Weck Incorporated, Princeton, N.J.

[21] Appl. No.: 142,351

[22] Filed: Dec. 28, 1987

Related U.S. Application Data

[63] Continuation of Ser. No. 936,056, Nov. 28, 1986, abandoned.

[30] Foreign Application Priority Data

Dec. 10, 1985 [GB] United Kingdom ............ 8530369

[51] Int. Cl.$^4$ ............................................. A61F 5/44
[52] U.S. Cl. .................................................. 604/338
[58] Field of Search ............................... 604/332–345

[56] References Cited

U.S. PATENT DOCUMENTS

| | | | |
|---|---|---|---|
| 3,331,370 | 7/1967 | Notley, Sr. | 604/342 |
| 3,339,546 | 9/1967 | Chen | 128/156 |
| 3,520,301 | 7/1970 | Fenton | 128/283 |
| 3,528,420 | 9/1970 | Nielson | 128/283 |
| 3,822,704 | 7/1974 | Nolen | 128/283 |
| 4,192,785 | 3/1980 | Chen et al. | 260/17.4 |
| 4,213,458 | 7/1980 | Nolen et al. | 128/283 |
| 4,393,080 | 7/1983 | Pawelchak et al. | 428/353 |
| 4,460,363 | 7/1984 | Steer et al. | 604/342 |
| 4,518,389 | 5/1985 | Steer et al. | 604/339 |
| 4,610,676 | 9/1986 | Schneider et al. | 604/339 |

FOREIGN PATENT DOCUMENTS

| | | | |
|---|---|---|---|
| 0098718 | 1/1984 | European Pat. Off. | |
| 2402243 | 7/1974 | Fed. Rep. of Germany | |
| 3417183 | 11/1985 | Fed. Rep. of Germany | 604/333 |
| 2115288 | 9/1982 | United Kingdom | |
| 2163350 | 2/1986 | United Kingdom | 604/338 |

Primary Examiner—Jerome L. Kruter
Attorney, Agent, or Firm—Donald J. Barrack; Robert E. Lee, Jr.

[57] ABSTRACT

An ostomy appliance intended for attachment to a peristomal area of a wearer includes a pad of medical-grade skin-attachable adhesive material, a first coupling element secured thereto, the element having a medically-extending flange attached to a surface of the pad and an upstanding rib of closed loop form constructed to couple with a couterpart (second) coupling element on a bag or pouch. An inner chute member is located radially within and adjacent to the first coupling element, the chute member having a substantially cylindrical wall covering the whole of the radially inner surface of the first coupling element. At one of its ends, the chute has a radially outwardly extending flange positioned so that it traps the chute member in position when the two coupling elements are coupled together.

1 Claim, 1 Drawing Sheet

OSTOMY COUPLING

This is a continuation of co-pending application Ser. No. 936,056 filed Nov. 28, 1986 now abandoned.

BACKGROUND OF THE INVENTION

This invention relates to a body-side ostomy appliance, for attachment to the peristomal area of a wearer, to permit removable attachment of a bag or pouch thereto.

Ostomy appliances are known in which a coupling element on the bag is engaged with one on an adhesive pad, the latter being stuck onto the wearer. One successful design is that shown in U.S. Pat. No. 4,460,363.

SUMMARY OF THE INVENTION

It is an aim of the invention to provide a design of ostomy appliance in which the chance of lodgment of faecal material in crevices of the appliance is greatly reduced, if, indeed, it is not wholly avoided.

According to the invention, an ostomy appliance intended for attachment to a peristomal area of a wearer includes a pad of medical-grade skin-attachable adhesive material, a first coupling element secured thereto, the element having a medically-extending flange attached to a surface of the pad and an upstanding rib of closed loop form constructed to couple with a counterpart (second) coupling element on a bag or pouch, and an inner chute member located radially within and adjacent to the first coupling element, the chute member having a substantially cylindrical wall covering the whole of the radially inner surface of the first coupling element and, at one of its ends, a radially outwardly extending flange positioned so that it traps the chute member in position when the two coupling elements are coupled together.

The present invention is applicable, with minor obvious modifications, to a variety of ostomy appliances, in particular those having a pair of interchangeable coupling elements, one on each of the pad and the pouch.

In a preferred version of the invention, a first coupling element has a rib and the second coupling element has a channel surrounding the stomal orifice, and the flange of the chute member is positioned to engage under the end of the radially inner channel wall.

The invention will be better understood from the following non-limiting description of an example thereof given with reference to the accompanying drawings.

DETAILED DESCRIPTION OF THE DRAWINGS

Figure 1:
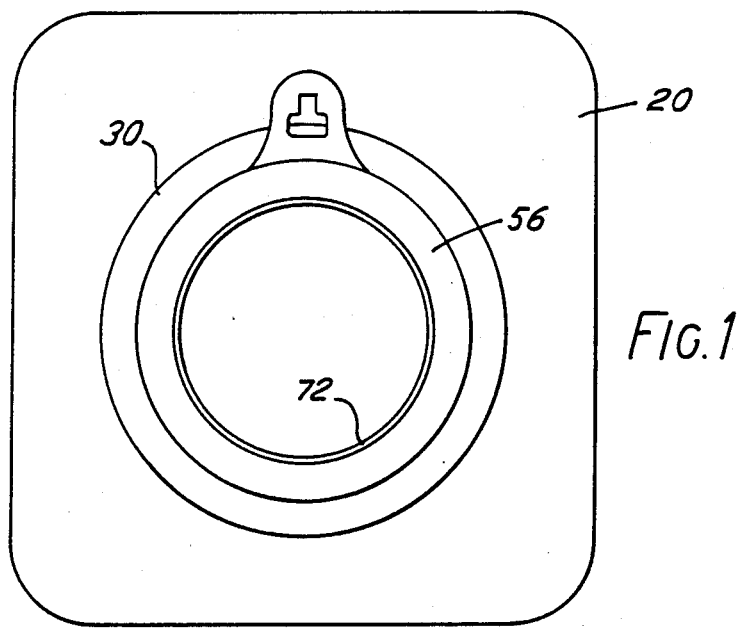
FIG. 1 is a front elevation view, omitting the bag or pouch, of two coupling elements together and including a chute member.
Figure 2:
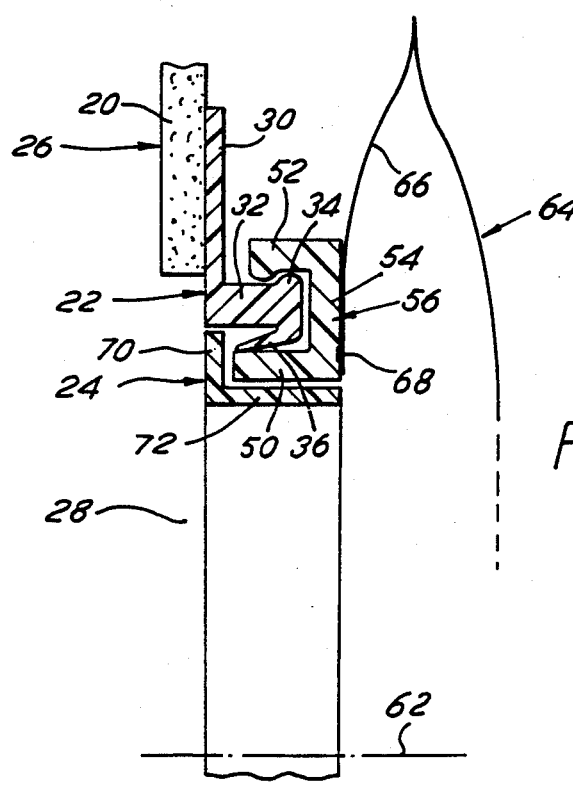
FIG. 2 is a vertical axial cross-section, with the bag or pouch indicated diagramatically, through an assembled ostomy appliance showing two coupling elements and a chute member.

The illustrated ostomy appliance according to the invention is intended for attachment to a peristomal area of a wearer and includes a pad 20 of medical grade skin-attachable adhesive material, a first coupling element 22, and a chute member 24. The pad 20 is substantially rectangular in form and may have on its rear surface 26 a stripable protective layer. As shown in FIG. 2, a central stomal orifice 28 has been cut therein, but as sold to the purchaser, the pad may constitute a substantially continuous rectangular patch.

The coupling element 22 comprises a radially outwardly extending flange 30 and a rib member 32 extending therefrom to encircle the stomal orifice. The rib 32 has a rim 34 thereon and an integral deflectable sealing strip 36. For a fuller description of the manner of operation of these parts attention is directed to the disclosure of U.S. Pat. No. 4,460,363.

The first coupling element 22 is intended to cooperate with a second coupling element 56. This is of channel form and is annular also surrounding the stomal orifice. The second coupling element 56 has an inner wall 50, an outer wall 52 and a channel base 54. The axis of the coupling member is indicated at 62. A pouch or bag is diagramatically indicated at 64. The bag wall 66 has a stomal aperture therein, and the wall 66 is secured to the second coupling element 56 in any suitable manner, for example by a plastics weld seam indicated at 68.

In accordance with the present invention, a chute member 24 is provided to guard against the possibility of faecal material becoming trapped in parts of the coupling. The preferred chute member 24 has a flange portion 70 which extends radially outwardly and underlies the assembled coupling elements 22 and 56 and the flange 70 is integral with a cylindrical tube or sleeve portion 72 which is located within and close to the inner wall 50 of the second coupling element 56. As can be seen best from FIG. 2, presence of the chute member 24 wholly prevents or greatly minimizes the chance of any faecal material becoming lodged in the parts of the coupling and the crevices and recesses necessarily defined thereby.

What is claimed is:

1. An ostomy appliance intended for attachment to a peristomal area of a wearer including a pad of medical-grade skin-attachable adhesive material, a first coupling element secured thereto, the element having an extending flange attached to a surface of the pad and an upstanding rib of closed loop form constructed to couple with a counterpart second coupling element on a bag or pouch having a stomal orifice, said second coupling element comprising inner and outer parallel spaced apart upstanding walls which form a channel surrounding the stomal orifice to accept the upstanding rib of the first coupling element and a separate inner chute member located radially within and adjacent to the first coupling element, the chute member having a substantially cylindrical wall covering the whole of the radially inner surface of the first coupling element and, at one of its ends, a radially outwardly extending flange positioned to be engaged under the end of the inner wall of said second coupling element said chute member is trapped when the two coupling elements are coupled together.

* * * * *

UNITED STATES PATENT OFFICE
CERTIFICATE OF CORRECTION

PATENT NO. : 4,892,530
DATED : January 9, 1990
INVENTOR(S) : Peter L. Steer

It is certified that error appears in the above-identified patent and that said Letters Patent is hereby corrected as shown below:

On the title page:

Assignee: Edward Weck Incorporated  -  this is incorrect. The correct Assignee is: E.R. Squibb and Sons, Inc. of Princeton, N.J.

Signed and Sealed this

Twenty-sixth Day of February, 1991

Attest:

HARRY F. MANBECK, JR.

*Attesting Officer*   *Commissioner of Patents and Trademarks*